(12) United States Patent
Haroche et al.

(10) Patent No.: US 6,905,865 B1
(45) Date of Patent: Jun. 14, 2005

(54) DETECTION OF A GENE, VATE, ENCODING AN ACETYLTRANSFERASE INACTIVATING STREPTOGRAMIN

(75) Inventors: Julien Haroche, Paris (FR); Jeanine Allignet, Nanterre (FR); Nevine El Solh, Vincennes (FR)

(73) Assignee: Institut Pasteur, Paris (FR)

( * ) Notice: Subject to any disclaimer, the term of this patent is extended or adjusted under 35 U.S.C. 154(b) by 622 days.

(21) Appl. No.: 09/628,693

(22) Filed: Jul. 28, 2000

Related U.S. Application Data

(60) Provisional application No. 60/146,141, filed on Jul. 30, 1999.

(51) Int. Cl.[7] .............................. C12N 1/20; C12N 9/10; C07H 21/02; C07K 1/00; C12Q 1/48
(52) U.S. Cl. ................... 435/252.3; 536/23.1; 536/23.2; 435/4; 435/6; 435/69.1; 435/71.1; 435/320.1; 435/193; 435/15; 530/350
(58) Field of Search .............................. 536/23.1, 23.2; 435/252.3, 320.1, 69.1, 71.1, 4, 6, 193, 15, 183, 440, 348, 410; 530/350

(56) References Cited

FOREIGN PATENT DOCUMENTS

WO          WO 98/59058     * 12/1998

OTHER PUBLICATIONS

Werner et al., Characterization of a new enterococcal gene, satG, encoding a putatie acetyltransferase conferring resistance to Streptogramin A compounds. Antimicrob. Agents Chemother. Jul. 1999, p. 1813–1814.*

Soltani et al. Identification of vat(E-3), a novel gene encoding resistance to quinupristin–dalfopristin in a strain of *Enterococcus faecium* from a hospital patient in the United Kingdom. Antimicrobial Agents and Chemotherapy, Feb. 2001, p. 645–646.*

Simjee et al. Variation witin the vat(E) allele of *Enterococcus faecium* isolates from retail poultry samples. Antimicrobial Agents and Chemotherapy, Oct. 2001, p. 2931–2932.*

U.S. Appl. No. 09/099932, filed Jun. 1988, Sohl et al., pending.

U.S. Appl. No. 09/446,301, filed Dec. 20, 1999, Solh et al., pending.

Welton et al., *Antimicrobial Agents and Chemotherapy*, 1998, 42(3) 705–708.

VanDenBogaard et al., *The New England Journal of Medicine* 337(21) 1558–1559 (1997).

VanDenBogaard *J. Antimicrob Chemother* 40, 454–456 (1997).

Rende–Fournier et al. *Antimicrobial Agents and Chemotherapy* 37(10) 2119–2125 (1993).

Murray et al., *Antimicrobial Agents and Chemotherapy* 41(1) 1–6 (1997).

Liassine et al. *Zbl. Bakt*, 286, 389–399 (1997).

Kreiswirth et al., *Nature* vol. 305, 709–712 (1983).

Allignet et al. *Antimicrobial Agents and Chemotherapy* 39(9) 2027–2036 (1995).

Allignet et al. *Antimicrobial Agents and Chemotherapy* 40(11) 2523–2528 (1996).

Moller et al. *APMIS* 106, 606–622 (1998).

* cited by examiner

*Primary Examiner*—Manjunath Rao
*Assistant Examiner*—Yong Pak
(74) *Attorney, Agent, or Firm*—Finnegan, Henderson, Farabow, Garrett & Dunner, L.L.P.

(57) ABSTRACT

A gene encoding an acetyltransferase inactivating streptogramin A was isolated from an *Enterococcus faecium* strain and sequenced. The gene, designated vatE, encodes a 23.775 kDa protein exhibiting 48.5 to 59.9% amino acid identity with four other enzymes with the same activity, Vat, VatB, VatC and SatA.

8 Claims, 3 Drawing Sheets

SEQ ID No. 17

```
   1  CCCTTTAAAG AGGGCTTTTA TATATTAATC ACAAATCACT TATCACAAAT
  51  CACAAGTGAT TTGTGATTGT TGATGATAAA ATAAGAATAA GAAGAAATAG
 101  AAAGAAGTGA GTGATTGTGG GAAATTTAGG CGCACAAAAA GAAAGAGTGT
                                                         -35
 151  GACAAAACAT GGTTATGCTA CATGTTTAAG GTAAAAATAG TTATGTCACA
                                                    -10
 201  ACTACTTATT TTTTTACCCA ATCTTCTAGA CTATAATTAA AATTAAATAA
                                    XbaI
                         ─────  M  T  I  P  D  A  N  A  I  V
 251  CTCAATTCGG AGGTACTAAC ATGACTATAC CTGACGCAAA TGCAATCTAT
             RBS           START
       H  N  S  A  I  K  E  V  V  F  I  K  N  V  I  K  S
 301  CATAACTCAG CCATCAAAGA GGTTGTCTTT ATCAAGAACG TGATCAAAAG
        DdeI                                       DpnI
       P  N  I  E  I  G  D  Y  T  Y  Y  D  D  P  V  N
 351  TCCCAATATT GAAATTGGGG ACTACACCTA TTATGATGAC CCAGTAAATC
          SspI
       P  T  D  F  E  K  H  V  T  H  H  Y  E  F  L  G  D
 401  CCACCGATTT TGAGAAACAC GTTACCCATC ACTATGAATT TCTAGGCGAC
       K  L  I  G  K  F  C  S  L  A  S  G  I  E  F  I
 451  AAATTAATCA TCGGTAAATT TTGTTCTCTC GCCAGTGGCA TTGAATTTAT
       M  N  G  A  N  H  V  M  K  G  I  S  T  Y  P  F
 501  CATGAACGGT GCCAACCACG TAATGAAAGG TATTTCGACT TATCCATTTA
                                             TaqI
       N  I  L  G  G  D  W  Q  Q  Y  T  P  E  L  T  D  L
 551  ATATATTAGG TGGCGATTGG CAACAATACA CTCCTGAACT GACTGATTTG
       P  L  K  G  T  V  V  G  N  D  V  W  F  G  Q  N  V
 601  CCGTTGAAAG GTGATACTGT AGTCGGAAAT GACGTGTGGT TTGGGCAAAA
       T  V  L  P  G  V  K  I  G  D  G  A  I  I  G  A
 651  TGTGACCGTC CTACCAGGCG TAAAAATAGG TGACGGTGCC ATTATCGGAG
       N  S  V  V  T  K  D  V  A  P  Y  T  I  V  G  G  N
 701  CAAATAGTGT TGTAACAAAA GACGTCGCTC CATATACAAT TGTCGGTGGC
       P  I  Q  L  I  G  P  R  F  E  P  E  V  I  Q  A  L
 751  AATCCAATTC AACTCATCGG ACCAAGATTT GAACCGGAAG TTATTCAAGC
                                                   XmnI
       E  N  L  A  W  W  N  K  D  I  E  W  I  T  A  N
 801  ATTAGAAAAT CTGGCATGGT GGAATAAAGA TATTGAATGG ATAACTGCTA
       N  V  P  K  L  M  Q  T  T  P  T  L  E  L  I  N  S
 851  ATGTTCCTAA ACTAATGCAA ACAACACCCA CACTTGAATT GATAAACAGT
       L  M  E  K  *
                   STOP
 901  TTAATGGAAA AATAAAAACA AAAAAGCCGT GCAAGCAATC CAAAAATGAT
 951  TGTTTACACG CCCTTTACTA TTTAGTGAAT CCAATTTATT AATAATAGAT
          HaeIII
1001  ATGATATACC AGTAAAAAAT ACACTAGCCA CCTCTGGCGG TACTCTACTC
1051  GTATATTTTA TTTACGACCT TCTGATGATA
```

FIGURE 1

```
SEQ ID No.19 Vat   LNLNNDHGPDPENILPIKGNRNLQFIKPTITN-ENILVGEYSYYDSKRG-ESFEDQVLYH
SEQ ID No.20 VatC  MKWQNQQGPNPEEIYPIEGNKHVQFIKPSITK-PNILVGEYSYYDSKDG-ESFESQVLYH
SEQ ID No.21 SatA  ------MGPNPMKMYPIEGNKSVQFIKPILEKLENVEVGEYSYYDSKNG-ETFDKQILYH
SEQ ID No.22 VatB  ----MKYGPDPNSIYPHEEIKSVCFIKNTITN-PNIIVGDYTYYSDVNGAEKFEEHVTHH
SEQ ID No.18 VatD  -----MTIPDANAIYHNSAIKEVVFIKNVIKS-PNIEIGDYTYYDDPVNPTDFEKHVTHH
                           *:.  :    .  : :  ***   :  .   *:  :*:*:**..   .    *:.:: :*

Vat   YEVIGDKLIIGRFCSIGPGTTFIMNGANHRMDG-STYPFHLFRMGWEKYMPSLKDLPLKG
             VatC  YELIGDKLILGKFCSIGPGTTFIMNGANHRMDG-STFPFNLFGNGWEKHTPTLEDLPYKG
             SatA  YPILNDKLKIGKFCSIGPGVTIIMNGANHRMDG-STYPFNLFGNGWEKHMPKLDQLPIKG
             VatB  YEFRGDKLVIGKFCAIAEGIEFIMNGANHRMNSITTYPFNIMGNGWEKATPSLEDLPFKG
             VatD  YEFLGDKLIIGKFCSLASGIEFIMNGANHVMKGISTYPFNILGGDWQQYTPELTDLPLKG
                   *  .  .***  :*:**::.  *    :******* *..  :*:**:::   .*::   *  *  :** **

Vat   DIEIGNDVWIGRDVTIMPGVKIGDGAIIAAEAVVTKNVAPYSIVGGNPLKFIRKRFSDGV
             VatC  NTEIGNDVWIGRDVTIMPGVKIGNGAIIAAKSVVTKNVDPYSVVGGNPSRLIKIRFSKEK
             SatA  DTIIGNDVWIGKDVVIMPGVKIGDGAIVAANSVVVKDIAPYMLAGGNPANEIKQRFDQDT
             VatB  DTVVGNDVWIGQNVTVMPGIQIGDGAIVAANSVVTKDVPPYRIIGGNPSRIIKKRFEDEL
             VatD  DTVVGNDVWFGQNVTVLPGVKIGDGAIIGANSVVTKDVAPYTIVGGNPIQLIGPRFEPEV
                   :   :*****:*::*.::**::**:***:.*::**.*::  **  :  ****  .  *    **.

Vat   IEEWLALQWWNLDMKIINENLPFIING--DIEMLKRKRKLLDDT
             VatC  IAALLKVRWWDLEIETINENIDCILNG--DIKKVKRS-------
             SatA  INQLLDIKWWNWPIDIINENIDKILDN--SIIREVIWKK-----
             VatB  IDYLLQIKWWDWSAQKIFSNLETLCSS--DLEKIKSIRD-----
             VatD  IQALENLAWWNKDIEWITANVPKLMQTTPTLELINSLMEK----
                   *         :  **:      .*   *:   :  .       :
```

US 6,905,865 B1

DETECTION OF A GENE, VATE, ENCODING AN ACETYLTRANSFERASE INACTIVATING STREPTOGRAMIN

This application claims the right to priority based on Provisional Patent Application No. 60/146,141 filed Jul. 30, 1999. The entire disclosure of Provisional Patent Application No. 60/146,141 is hereby incorporated by reference.

BACKGROUND OF THE INVENTION

This invention relates to the discovery of a new gene, vatE, encoding an acetyltransferase inactivating streptogramin A, which is widely distributed in virginiamycin-resistant *enterococcus faecium* strains.

Streptogramin, virginiamycin, pristinamycin, and synergistin are produced by *streptomyces*, and consist of synergistic mixtures of two chemically different molecules: A and B compounds (10) In some European countries and in Algeria, these mixtures are used both orally and topically, mostly against staphylococcal infections. Virginiamycin is used as growth promoter in animal feed in Europe and in the U.S.A. Virginiamycin-resistant *Enterococcus faecium* are prevalent in fecal and intestinal samples from turkeys, pigs, broilers, and farmers in Europe and America (1, 14, 19, 20). Since bacteria can be transferred via food from animals to humans, this is alarming, in particular because quinupristin/dalfopristin (J. Antimicrob. Agents Chemother., 1992, 30[suppl.30]), an injectable mixture of semi-synthetic streptogramins soon to be commercialized (Synercid), is expected to be widely used, mainly to treat vancomycin-resistant *E. faecium* infections.

The satA gene (18) encoding an acetyltransferase inactivating A compounds was isolated from an *E. faecium* plasmid. It was found in only 29% of the 140 tested *E. faecium* strains isolated in Dutch and Danish farms and resistant to the mixtures (13, 14). Five of the *E. faecium* strains isolated in Denmark harbored a large plasmid conferring resistance to the mixture and which was transferable by filter mating experiments to an *E. faecium* recipient (14). None of the transconjugants harboring these plasmids carried satA, vat, vatB, vga, or vgaB (14). These results suggested that the *E. faecium* strains contained other unidentified streptogramin A resistance gene(s). Thus, there continues to exist a need in the art for the identification of new genes specific for *Enterococcus faecium* resistant to streptogramin A and related compounds.

SUMMARY OF THE INVENTION

Accordingly, this invention aids in fulfilling this need in the art by providing a new gene, vatE, encoding an acetyltransferase inactivating Streptogramin A, which is widely distributed in virginiamycin-resistant *Enterococcus faecium* strains. In particular, this invention provides a purified peptide-comprising the complete amino acid sequence (SEQ ID NO:1) encoded by the vatE gene. This invention also provides polypeptide fragments derived from SEQ ID NO:1 containing at least 10 amino acids. The fragments can be common to all virginiamycin A acetyl transferases as shown on SEQ ID NOS:5, 6, 7, and 8. The fragments according to the invention can be specific of as shown on SEQ ID NOS:9, 10, 11, and 12.

This invention additionally provides a purified polynucleotide comprising the complete nucleic acid sequence of the vatE gene (SEQ ID NO:2). This invention also provides nucleic acid fragments derived from SEQ ID NOS:3 and 4 containing 15 to 40 nucleotides as primers F and R. For example, the fragments are those corresponding to nucleotides No. 899 to 878 and to nucleotides No. 354 to nucleotide 378. (FIG. 1)

In addition, two primers have been selected in order to obtain, after using an amplification technique and after cloning the amplified sequence, the complete gene of vatE capable of being expressed in *Staphylococcus aureus* (strain No. 4220 described by KREISWIRTH et al. in Nature 1983, Vol. 306, pp. 709–712]. These primers are shown in SEQ ID NOS:13 and 14 as vatEA and vatEB. The vatEA is from nucleotide 98 to nucleotide 120 (FIG. 1). The vatEB is from nucleotide 982 to nucleotide 957 (FIG. 1).

In SEQ ID NOS:13 and 14, an artificial site was created if comparing with the original sequence in FIG. 1 at nucleotides No. 107 and 109 where G was replaced by T and G was replaced by C, respectively. An EcoRI site was then produced in the first primer. In the same manner, in SEQ ID NOS:3 and 4, at nucleotide No. 362, A replaces G (as in the original sequence) and at nucleotide 367, C replaces G (as in the original sequence). A new EcoRI site was created. In the second primer of SEQ ID NOS:3 and 4, a new EcoRI site was created by replacing at nucleotide No. 891 G by C and on the complementary strand (as shown) the base C is replaced by G.

This invention also provides a composition comprising purified polynucleotide sequences including at least one nucleotide sequence of the genes selected from the group consisting of synthetic polynucleotides or fragments of genes or cDNA of vatE useful for the detection of resistance to streptogramin A and related compounds. The gene vatE was obtained from a HindIII fragment of 5 kb prepared from *enterococcus faecium* genome (strain K14) after digestion by HindIII restriction enzyme. The Hind III fragment hybridizes with an amplicon containing two degenerated or consensus primers referred to as M and N, which are defined as SEQ ID NOS:5, 6, 7, and 8. This amplicon has 147 nucleotides. The amplicon or the two degenerated primers (M and N) can be used for the preparation of DNA chips as taught in PCT applications No. WO95.11.995 and No. WO 97.02.357. The sequences upstream and downstream of this amplicon were obtained.

The DNA fragment containing the vatE gene including the amplicon is shown in FIG. 1. A region having in this said fragment, the possible properties of a bacterial promoter activity is located as follows in FIG. 1. Its sequence is:

```
                                             -35
                                           TGTCACA
                                             -10
201 ACTACTTATT TTTTTACCCA ATCTTCTAGA CTATAAT
                                    XbaI
(SEQ ID NO:16)
```

Additionally, the invention includes a purified polynucleotide that hybridizes specifically under stringent conditions with a polynucleotide of SEQ ID NOS: 2, 3, 4, 5, 6, 7, 8, 9, 10, 11, or 12.

The invention further includes polynucleotide fragments comprising at least 10 nucleotides capable of hybridization under stringent conditions with any one of the nucleotide sequences enumerated above.

In another embodiment of the invention, a recombinant DNA sequence comprising at least one nucleotide sequence enumerated above and under the control of regulatory elements that regulate the expression of resistance to antibiotics of the streptogramin family in a defined host is provided. The amplified complete gene of vatE, including the amplicon and the promoter, is shown in SEQ ID NO:15.

Furthermore, the invention includes a recombinant vector comprising the recombinant DNA sequence noted above, wherein the vector comprises the plasmid pIP 1801 contained in *E. coli*. The recombinant strain has been deposited at the collection C.N.C.M. in Paris, France, under the accession number I-2247 on Jul. 7, 1999.

The invention also includes a recombinant cell host comprising a polynucleotide sequence enumerated above or the recombinant vector defined above.

In still a further embodiment of the invention, a method detecting bacterial strains that contain the polynucleotide sequences set forth above is provided.

Additionally, the invention includes kits for the detection of the presence of bacterial strains that contain the polynucleotide sequences set forth above.

The invention also contemplates antibodies recognizing peptide fragments or polypeptides encoded by the polynucleotide sequences enumerated above.

Still further, the invention provides for a screening method for active antibiotics and/or molecules for the treatment of infections due to Gram-positive bacteria, particularly enterococci, based on the detection of activity of these antibiotics and/or molecules on bacteria having the resistance phenotype to streptogramins.

BRIEF DESCRIPTION OF THE DRAWINGS

This invention will be more fully described with reference to the drawings in which:

FIG. 1 discloses the complete nucleotide and amino acid sequences of vatE. In this Figure are also represented the upstream and downstream regions of the vatE gene.

FIG. 2 is a comparison between the sequences of vatE protein and four acetyltransferase enzymes already published.

DETAILED DESCRIPTION OF THE INVENTION

Figure 3:
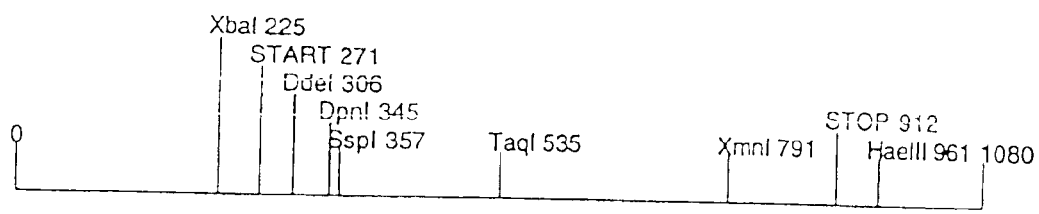
FIG. 3 is a restriction map of the insert of 1080 bp contained in the plasmid deposited in *E. coli* at C.N.C.M. I-2247.

The present invention pertains to polynucleotides derived from *Enterococcus faecium* genes encoding resistance to streptogramin A and chemically related compounds. This invention also relates to the use of the polynucleotides as oligonucleotide primers or probes for detecting *Enterococcus faecium* strains that are resistant to streptogramin A and related compounds in a biological sample.

In another embodiment, the present invention is directed to the full length coding sequences of the *Enterococcus faecium* genes encoding resistance to streptogramin A and to the polypeptides expressed by these full length coding sequences.

Further, this invention relates to the use of the expressed polypeptides to produce specific monoclonal or polyclonal antibodies that serve as detection means in order to character any *Enterococcus faecium* strain carrying genes encoding resistance to streptogramin A and chemically related compounds.

The present invention is also directed to diagnostic method for detecting specific strains of *Enterococcus faecium* expected to be contained in a biological sample. The diagnostic methods use the oligonucleotide probes and primers as well as the antibodies of the invention.

More particularly, it has now been determined that bacteria from the *Enterococcus faecium* genus carry a vatE gene, which confers resistance to streptogramin A. A gene encoding an acetyltransferase inactivating streptogramin A was isolated from an *Enterococcus faecium* strain and sequenced. The gene, designated vatE, encodes a 23,775 kDa protein exhibiting 48.5 to 59.9% amino acid identity with four other enzymes with the same activity, vat, vatB, vatC, and satA. The calculation of the percentage of identity was made by using the program gap of GCG software (version 9.1). The parameters are chosen as follows:

a) for amino acid comparisons:
  gap penalty: 12
  gap extension penalty: 4
  length: the sequence to be compared in SEQ ID NO:1 having 213 amino acids.
b) for nucleotide comparisons:
  gap penalty: 50
  gap extension penalty: 3.

FIG. 2 shows the comparative amino acid alignments of vatE with four virginiamycin A acetyl transferase proteins. The satB protein is from *Enterococcus*, and vat, vatB, and vatC are from *Staphylococcus*.

Novel polynucleotides corresponding to the vatE gene from various strains of *Enterococcus faecium* have been isolated and sequenced. These polynucleotides include SEQ ID NO:2. By "polynucleotides" according to the invention is meant the sequence referred to as SEQ ID NO:2, and the complementary sequences and/or the sequences of polynucleotides that hybridize to the referred sequences in high stringent conditions (hybridization in a mixture containing 5×SSPE, 5× Denhart solution, 0.5% SDS (w/v) and 100 μg/ml salmon sperm DNA]. The membrane on which is hybridized the DNA, is washed 2 times during 10 minutes, in 2×SSPE, 0.1% SDS (w/v) at room temperature and then the membrane (or the filter) is immersed in a solution of 1×SSPE, 0.1% SDS (w/v) during 15 minutes at 68° C. and finally in a solution of 1×SSPE, 0.1% SDS (w/v) during 15 minutes at 68° C. The polynucleotides according to the invention are used for detecting *Enterococcus faecium* strains carrying a gene encoding resistance to streptogramin A.

By "active molecule" according to the invention is meant a molecule capable of inhibiting the activity of the purified polypeptide as defined in the present invention or capable of inhibiting the bacterial culture of *Enterococcus faecium* strains.

Thus, the polynucleotides of SEQ ID NO:2 and its fragment can be used to select nucleotide primers notably for an amplification reaction, such as the amplification reactions further described. PCR is described in the U.S. Pat. No. 4,683,202 granted to Cetus Corp. The amplified fragments may identified by agarose or polyacrylamide gel electrophoresis, or by a capillary electrophoresis, or alternatively by a chromatography technique (gel filtration, hydrophobic chromatography, or ion exchange chromatography). The specificity of the amplification can be ensured by a molecular hybridization using as nucleic probes the polynucleotides derived from SEQ ID NO:2 and its fragments, oligonucleotides that are complementary to these polynucleotides or fragments thereof, or their amplification products themselves.

Amplified nucleotide fragments are useful as probes in hybridization reactions in order to detect the presence of one polynucleotide according to the present invention or in order detect the presence of a bacteria of *Enterococcus faecium* strain carrying genes encoding resistance to streptogramin A, in a biological sample. This invention also provides, the amplified nucleic acid fragments ("amplicons") defined herein above. These probes and amplicons can be radioactively or non-radioactively labeled, using for example enzymes or fluorescent compounds.

Preferred nucleic acid fragments that can serve as primers according to the present invention are the following in the FIG. 1:

```
PRIMER F    5'-CAATATTGGAATTCGGGACTACACC-3'    (SEQ ID NO:3)
                    EcoRI
            nt 354          nt 378 gene vatE
PRIMER R    5'-CTGTTTATGAATTCAAGTGTGG-3'       (SEQ ID NO:4)
                    EcoRI
            nt 899    nt 878 gene valE
```

The primers can also be used as oligonucleotide probes to specifically detect a polynucleotide according to the invention.

Other techniques related to nucleic acid amplification can also be used and are generally preferred to the PCR technique. The Strand Displacement Amplification (SDA) technique (Walker et al., 1992) is an isothermal amplification technique based on the ability of a restriction enzyme to cleave one of the strands at a recognition site (which is under a hemiphosphorothioate form), and on the property of a DNA polymerase to initiate the synthesis of a new strand from the 3' OH end generated by the restriction enzyme and on the property of this DNA polymerase to displace the previously synthesized strand being localized downstream.

The SDA amplification technique is more easily performed than PCR (a single thermostated water bath device is necessary and is faster than the other amplification methods. Thus, the present invention also comprises using the nucleic acid fragment according to the invention (primers) in a method of DNA or RNA amplification according to the SDA technique. The polynucleotides of SEQ ID NO:2 and its fragments, especially the primers according to the invention, are useful as technical means for performing different target nucleic acid amplification methods such as:

TAS (Transcription-based Amplification System), described by Kwoh et al. in 1989;

SR (Self-Sustained Sequence Replication), described by Guatelli et al. In 1910;

NASBA (Nucleic acid Sequence Based Amplification), described by Kievitis et al. in 1991; and TMA (Transcription Mediated Amplification).

The polynucleotides of SEQ ID NO:2 and its fragments, especially the primers according to the invention, are also useful as technical means for performing methods for amplification or modification of a nucleic acid used as a probe, such as:

LCR (Ligase Chain Reaction), described by Landegren et al. in 1988 and improved by Barany et al. in 1991, who employ a thermostable ligase;

RCR (Repair Chain Reaction), described by Segev et al. 1992;

CPR (Cycling Probe Reaction), described by Duck et al. in 1990; and

Q-beta replicase reaction, described by Miele et al. in 1983 and improved by Chu et al. in 1986, Lizardi et al. in 1988 and by Burg et al. and Stone et al. in 1996.

When the target polynucleotide to be detected is RNA, for example mRNA, a reverse transcriptase enzyme can be used before the amplification reaction in order to obtain a cDNA from the RNA contained in the biological sample. The generated cDNA can be subsequently used as the nucleic acid target for the primers or the probes used in an amplification process or a detection process according to the present invention.

Nucleic probes according to the present invention are specific to detect a polynucleotide of the invention. By "specific probes" according to the invention is meant any oligonucleotide that hybridizes with the polynucleotide of SEQ ID NO:2, and which does not hybridize with unrelated sequences. Preferred oligonucleotide probes according to the invention are SEQ ID NOS:5, 6, 7, or 8 or SEQ ID NOS:3 or 4.

In a specific embodiment, the purified polynucleotides according to the present invention encompass polynucleotides having at least 80% identity in their nucleic acid sequences with polynucleotide of SEQ ID NO:2. By percentage of nucleotide homology according to the present invention is intended a percentage of identity between the corresponding bases of two homologous polynucleotides, this percentage of identity being purely statistical and the differences between two homologous polynucleotides being located at random and on the whole length of said polynucleotides. The calculation was made according to the software GCG and the program "gap."

The oligonucleotide probes according to the present invention hybridize specifically with a DNA or RNA molecule comprising all or part of the polynucleotide of SEQ ID NO:2 under stringent conditions. As an illustrative embodiment, the stringent hybridization conditions used in order to specifically detect a polynucleotide according to the present invention are advantageously the following:

Prehybridization and hybridization are performed at 68° C. a mixture containing:

5×SSPE (1×SSPE is 0.3 M NaCl, 30 mM tri-sodium citrate

5× Denhardt's solution 0.5% (w/v) sodium dodecyl sulfate (SDS); and

100 $\mu$g ml$^{-1}$ salmon sperm DNA

The washings are performed as follows:

Two washings at laboratory temperature for 10 min. in the presence of 2×SSPE and 0.1% SDS;

One washing at 68° C. for 15 min. in the presence of 1×SSPE, 0.1% SDS; and

One washing at 68° C. for 15 min. in the presence of 0.1×SSPE and 0.1% SDS.

The non-labeled polynucleotides or oligonucleotides of the invention can be directly used as probes. Nevertheless, the polynucleotides or oligonucleotides are generally labeled with radioactive element ($^{32}$P, $^{35}$S, $^{3}$H, $^{125}$I) or by a non-isotopic molecule (for example, biotin, acetylaminofluorene, digoxigenin, 5-bromodesoxyuridin, fluorescein) in order to generate probes that are useful for numerous applications. Examples of non-radioactive labeling of nucleic acid fragments are described in the French Patent No. FR 78 10975 or by Urdea et al. or Sanchez Pescador et al. 1988.

Other labeling techniques can also be used, such as those described in the French patents 2 422 956 and 2 518 755.

The hybridization step may be performed in different ways (Matthews et al. 1988). A general method comprises immobilizing the nucleic acid that has been extracted from the biological sample on a substrate (nitrocellulose, nylon, polystyrene) and then incubating, in defined conditions, the target nucleic acid with the probe. Subsequent to the hybridization step, the excess amount of the specific probe is discarded, and the hybrid molecules formed are detected by an appropriate method (radioactivity, fluorescence, or enzyme activity measurement).

Advantageously, the probes according to the present invention can have structural characteristics such that they allow signal amplification, such structural characteristics being, for example, branched DNA probes as those described by Urdea et al. in 1991 or in the European Patent No. 0 225 807 (Chiron).

In another advantageous embodiment of the present invention, the probes described herein can be used as "capture probes", and are for this purpose immobilized on a substrate in order to capture the target nucleic acid contained in a biological sample. The captured target nucleic acid is subsequently detected with a second probe, which recognizes a sequence of the target nucleic acid that is different from the sequence recognized by the capture probe.

The oligonucleotide fragments useful as probes or primers according to the present invention can be prepared by cleavage of the polynucleotide of SEQ ID NO:2 by restriction enzymes, as described in Sambrook et al. in 1989. Another appropriate preparation process of the nucleic acids of the invention containing at most 200 nucleotides (or 200 bp if these molecules are double-stranded) comprises the following steps:

synthesizing DNA using the automated method of beta-cyanethylphosphoramidite described in 1986;

cloning the thus obtained nucleic acids in an appropriate vector; and purifying the nucleic acid by hybridizing to an appropriate probe according to the present invention.

A chemical method for producing the nucleic acids according to the invention, which have a length of more than 200 nucleotides (or 200 bp if these molecules are double-stranded) comprises the following steps:

assembling the chemically synthesized oligonucleotides having different restriction sites at each end;

cloning the thus obtained nucleic acids in an appropriate vector; and purifying the nucleic acid by hybridizing to an appropriate probe according to the present invention.

The oligonucleotide probes according to the present invention can also be used in a detection device comprising a matrix library of probes immobilized on a substrate, the sequence of each probe of a given length being localized in a shift of or several bases, one from the other, each probe of the matrix library thus being complementary to a distinct sequence of the target nucleic acid. Optionally, the substrate of the matrix can be a material able to act as an electron donor, the detection of the matrix positions in which hybridization has occurred being subsequently determined by an electronic device. Such matrix libraries of probes and methods of specific detection of a target nucleic acid are described in the European patent application No. 713 016, or PCT Application No. WO 95 33846, or also PCT Application No. WO 95 11995 (Affymax Technologies), PCT Application No. WO 97 02357 (Affymetrix Inc.), and also in U.S. Pat. No. 5,202,231 (Drmanac), said patents and patent applications being herein incorporated by reference.

The present invention also pertains to a family of recombinant plasmids containing at least a nucleic acid according to the invention. According to an advantageous embodiment, a recombinant plasmid comprises a polynucleotide of SEQ ID NO:2 or nucleic acid fragment thereof. More specifically, the following plasmid is part of the invention: pIP1801 or its fragments. Said fragments are derived from the use of restriction enzymes according to the restriction map of the gene vatE, as shown in FIG. 3.

The present invention is also directed to the full length coding sequences of the vatE gene from *Enterococcus faecium* available using the purified polynucleotides according to the present invention, as well as to the polypeptide enzymes encoded by these full length coding sequences. In a specific embodiment of the present invention, the full length coding sequence of the vatE gene is isolated from a plasmid or cosmid library of the genome of *Enterococcus faecium* that has been screened with the oligonucleotide probe according to the present invention. The selected positive plasmid or cosmid clones hybridizing with the oligonucleotide probes of the invention are then sequenced in order to characterize the corresponding full length coding sequence, and the DNA insert of interest is then cloned in an expression vector conferring resistance to streptogramin A and related compounds.

A suitable vector for the expression in bacteria and in particular in *E. coli*, is the pQE-30 vector (QIAexpress) that allows the production of a recombinant protein containing a 6xHis affinity tag. The 6xHis tag is placed at the C-terminus of the recombinant polypeptide ATP binding motif conferring resistance to streptogramin A and related compounds.

The polypeptides according to the invention can also be prepared by conventional methods of chemical synthesis, either in a homogenous solution or in solid phase. As an illustrative embodiment of such chemical polypeptide synthesis techniques the homogenous solution technique described by Houbenweyl in 1974 may be cited.

The polypeptide conferring resistance to streptogramin A and related compounds is useful for the preparation of polyclonal or monoclonal antibodies that recognize the polypeptides or fragments thereof. The monoclonal antibodies can be prepared from hybridomas according to the technique described by Kohler and Milstein in 1975. The polyclonal antibodies can be prepared by immunization of a mammal, especially a mouse or a rabbit, with a polypeptide according to the invention that is combined with an adjuvant, and then by purifying specific antibodies contained in the serum of the immunized animal on an affinity chromatography column on which has previously been immobilized the polypeptide that has been used as the antigen.

Consequently, the invention is also directed to a method detecting specifically the presence of a polypeptide according to the invention in a biological sample. The method comprises:

a) bringing into contact the biological sample with an antibody according to the invention; and b) detecting antigen-antibody complex formed.

Also part of the invention is a diagnostic kit for in vitro detecting the presence of a polypeptide according to the present invention in a biological sample. The kit comprises:

a polyclonal or monoclonal antibody as described above, optionally labeled; and a reagent allowing the detection of the antigen-antibody complexes formed, wherein the reagent carries optionally a label, or being able to be recognized itself by a labeled reagent, more particularly in the case when the above-mentioned monoclonal or polyclonal antibody is not labeled by itself.

Indeed, the monoclonal or polyclonal antibodies according to the present invention are useful as detection means in order to identify or characterize a *Staphylococcal* strain carrying gene encoding resistance to streptogramin A.

The invention also pertains to:

A purified polypeptide or a peptide fragment having at least 10 amino acids, which is recognized by antibodies directed against a polynucleotide sequence conferring resistance to streptogramin and related compounds, corresponding to a polynucleotide sequence according to the invention.

A polynucleotide comprising the full length coding sequence of a *Enterococcus faecium* streptogramin A resistant gene containing a polynucleotide sequence according to the invention.

A monoclonal or polyclonal antibody directed against a polypeptide or a peptide fragment encoded by the polynucleotide sequences according to the invention.

A method of detecting the presence of bacterium harboring the polynucleotide sequences according to the invention in a biological sample comprising:

a) contacting bacterial DNA of the biological sample with a primer or a probe according to the invention, which hybridizes with a nucleotide sequence encoding resistance to streptogramins;

b) amplifying the nucleotide sequence using said primer or said probe; and c) detecting the hybridized complex formed between said primer or probe with the DNA.

A kit for detecting the presence of bacterium having resistance to streptogramin A and harboring the polynucleotide sequences according to the invention in a biological sample, said kit comprising:

a) a polynucleotide probe according to the invention; and b) reagents necessary to perform a nucleic acid hybridization reaction.

A kit for detecting the presence of bacterium having resistance to streptogramin A and harboring the polynucleotide sequences according to the invention in a biological sample, said kit comprising:

a) a polynucleotide probe according to the invention; and b) reagents necessary to perform a nucleic acid hybridization reaction.

A method of screening active antibiotics for the treatment of the infections due to Gram-positive bacteria, comprising the steps of:

a) bringing into contact a Gram-positive bacteria having a resistance to streptogramin A and related compounds and containing the polynucleotide sequences according to the invention with the antibiotic; and b) measuring an activity of the antibiotic on the bacteria having a resistance to streptogramins and related compounds.

A method of screening for active synthetic molecules capable of penetrating into a bacteria of the family of *enterococcus*, wherein the inhibiting activity of these molecules is tested on at least a polypeptide encoded by the polynucleotide sequences according to the invention comprising the steps of:

a) contacting a sample of said active molecules with the bacteria;

b) testing the capacity of the active molecules to penetrate into the bacteria and the capacity of inhibiting a bacterial culture at various concentration of the molecules; and c) choosing the active molecule that provides an inhibitory effect of at least 80% on the bacterial culture compared to an untreated culture.

An in vitro method of screening for active molecules capable of inhibiting a polypeptide encoded by the polynucleotide sequences according to the invention, wherein the inhibiting activity of these molecules is tested on at least said polypeptide, said method comprising the steps of:

a) extracting a purified polypeptide according to the invention;

b) contacting the active molecules with said purified polypeptide;

c) testing the capacity of the active molecules, at various concentrations, to inhibit the activity of the purified polypeptide; and d) choosing the active molecule that provides an inhibitory effect of at least 80% on the activity of the said purified polypeptide.

In the inactivation by the O-acetylation of virginiamycin A mediated by vatE, the donor of acetyl group is probably acetyl coenzyme A. The acetylation reduced coenzyme A can react with 5,5'-dithio-bis 2 nitrobenzoate (DTNB) to yield 5 thio 2 nitrobenzoate with a 1:1 stoichiometry. The 5 thio 2 nitrobenzoate is yellow and has a high extinction coefficient (E=00136 $mM^{-1}$ $cm^{-1}$) at λ412 nm. Therefore, the measurement of its appearance can be recorded by a spectrophotometer with great sensitivity.

As examples there are disclosed hereinafter the detection of chloramphenicol acetyl transferase activity. Similar conditions may be used for the detection of virginiamycin A activity to yield 5-thio-2-nitrobenzoate with a stoichiometry. The thio-2-nitrobenzoate is yellow and has a high extinction coefficient (00136 $mM^{-1}$ $cm^{-1}$) at λ412 nm. Therefore, the measurement of its appearance can be recorded spectrophotometrically with great sensitivity.

Materials

Bacterial strain(s) to be tested.

Mueller-Hinton (MH) broth (Gram-negative bacteria) or brain heart infusion (BHI) broth (Gram-positive cocci)

50 ml centrifuge tubes

Eppendorf tubes

Low speed centrifuge

Refrigerated bench centrifuge

Sonicator

Double beam recording spectrophotometer equipped with a water-jacketed cuvette

Tris-Cl 1M (pH 6.0)

Tris-Cl 1M (pH 7.8)

Dithiothreitol (DTT) 0.01 M

TDTT buffer: Tris-Cl50 mM (pH 7.8) DTT 20 μM

Acetyl coenzyme A (CoASAc) 10 mM (PH 6.0): dissolve 8.2 mg of CoASAc in 1 ml of 5 mM Tris-Cl (pH 6.0). This solution can be stored frozen for 1 year in aliquots (100 μl).

5,5'-dithiobis-2-nitrobenzoic acid (DTNB) 10 mM (PH 7.8): dissolve 20 μg of DTNB in 0.5 ml of 1 M Tris-C1 (pH 7.8) and add 4.5 ml of distilled water. This solution should be make fresh each time.

Reaction mixture: CoASAc (10 mM, pH 6.0): 100 μl
DTNB (10 mM, pH 7.8): 500 μl
Tris-Cl (1 M, pH 7.8): 920 μl
$H_2O$ up to 10 ml This volume is sufficient for 15 reactions.

Chloramphenicol (Cm) 10 mM (pH 7.8): dissolve 3.2 mg of Cm in 1 ml of 100 mM Tris-Cl (pH 7.8). Heat 10 min in water bath at 100° C. Store at +4° C.

Protocol

Day 1

1. Inoculate separately 5 ml of MH broth with bacterial strains to be tested. Grow overnight at 37° C. with moderate shaking.

Day 2

2. Inoculate separately 35 ml of MH broth with 1 ml of each overnight culture. Grow at 37° C. with moderate shaking until the $OD_{600nm}$ is 0.8.
3. Centrifuge the cells (8000 rpm, 10 min, 4° C.). Discard the supernatant and wash the pellet in 1 ml of TDDT buffer. Centrifuge again and resuspend the pellet in 1 ml of the same buffer.
4. Sonicate the cells at 4° C. with 5×30 s pulses with 30 s rest in between.
5. Centrifuge the samples in an Eppendorf centrifuge (15000 rpm, 10 min, 4° C.) to remove cell debris.
6. Transfer supernatants (S20) to other Eppendorf tubes and keep on ice until assayed. If the CAT assay is not performed on the same day, freeze the samples at −20° C. The CAT activity can be retained frozen for at least one month.
7. Pour 600 μl of reaction mixture to reference cuvette and sample cuvettes equilibrated at 37° C. in a double beam recording spectrophotometer. Let stand 2 min and adjust $OD_{412}$ nm to 0.
8. Add 20 μl of S20 to sample cuvettes, mix well, and record $OD_{412nm}$ for 1–2 min to determine the background CAT activity.
9. When a constant slope is obtained, add 10 μl of Cm to cuvettes, mix well and record the increase in absorbance ($OD_{412}$ nm) for about 5 min. If the CAT activity is too high, a more reliable measure of activity can be obtained by diluting the S20.
10. Measure the amount of protein in the S20.
11. Determine the slope ($OD_{412\ nm}$/min) before and after adding Cm and then subtract the background slope from the sample slope. The CAT enzyme specific activity expressed in nmole/min/mg is Δ $OD_{412nm}$/0.0136/mg protein [0.0136 being the extinction coefficient ($mM^{-1}cm^{-1}$ λ412 nm) of 5-thio-2-nitrobenzoate].

Notes

Since the formation of 5-thio-2-nitrobenzoate is accompanied by the appearance of a yellow coloration, CAT activity can be qualitatively appreciated de visu in step 9.

The crude extracts (S20) obtained from certain bacterial genera contain high thioesterase activity that may mask that of CAT since it also catalyzes the formation of reduced coenzyme A. On the other hand, DTNB was reported to inhibit certain CTAs from Gram-negative bacteria. In both cases, partial purification of the enzyme or the use of an alternate procedure is necessary to overcome these problems. Different methods for convenient CAT assays based on labeled acetyl coenzyme A (or butyryl coenzyme A) for acyl donor are available.

Chloramphenicol analogs, such as 3'-desoxychloramphenicol, can be used to induce CAT expression in Gram-positive bacteria. This compound is not acetylated by CATs (free inducer) and has little effect on protein synthesis.

Medium containing carbohydrates other than glucose may be used for the growth of Gram-negative bacteria to avoid catabolic repression.

If an active molecule for inhibiting the activity of the bacterial enzyme (acetyl transferase) is added to a culture medium containing the resistant strain, the acetyl co-enzyme A present in said medium is not degradated. If the molecule to be tested is not active on the resistant bacteria, the amount of acetyl co-enzyme A decreases.

A test for screening the inhibiting activity of a molecule, for example, a new antibiotic or a new antibacterial agent, can comprise the following steps:

a) adding purified active acetyl transferase vatE in a solution containing virginiamycin A at various concentrations, acetyl co-enzyme A, b) adding the molecule to be tested at various concentrations, c) revealing the presence of acetyl co-enzyme A activity and quantifying said acetyl coenzyme A, if necessary, and d) comparing the quantification of acetyl coenzyme A with a control without the new molecule.

A composition of a polynucleotide sequence encoding resistance to streptogramins and related compounds, or inducing resistance in Gram-positive bacteria, wherein said composition comprises a nucleotide sequence corresponding to the resistance phenotype of the plasmid pIP1807 deposited with the C.N.C.M. under the Accession No. I-2247 on Jul. 7, 1999.

A method of detecting the presence of bacterium harboring the polynucleotide sequences according to the invention in a biological sample, said method comprising the steps of:

a) contacting said sample with an antibody according to the invention that recognizes a polypeptide encoded by said polynucleotide sequences; and b) detecting said complex.

A diagnostic kit for in vitro detecting the presence of bacterium harboring the polynucleotide sequences according to invention in a biological sample, said kit comprising:

a) a predetermined quantity of monoclonal or polyclonal antibodies according to the invention;

b) reagents necessary to perform an immunological reaction between the antibodies and a polypeptide encoded by said polynucleotide sequences; and c) reagents necessary for detecting said complex between the antibodies and the polypeptide encoded by said polynucleotide sequences.

Plasmids containing the polynucleotides from *Enterococcus faecium*, which confer streptogramin A resistance have been inserted into vectors, which have been deposited at the Collection Nationale de Cultures de Microorganismes ("C.N.C.M.") Institut Pasteur, 28, rue du Docteur Roux, 75724 Paris Cedex 15 France on Jul. 7, 1999, as follows:

| Plasmid | Accession No. |
| --- | --- |
| pIP1801 | I-2247 |

This invention will now be described in greater detail in the following Example.

EXAMPLE

A collection of 51 *E. faecium* strains was studied for resistance to streptogramins. The strains were isolated from fecal samples from poultry (n=22), pigs (n=5), farmers (n=19) and (sub)urban residents (n=5) in the Netherlands (Table 1). satA was previously found in 19 strains and vgb in a single strain by PCR (14). The *E. faecium* strains were analyzed for nucleotide sequences hybridizing at high stringency (65° C.) with the eight genes previously found in staphylococcal and enterococcal plasmids conferring resistance to the mixtures: satA (18), vat (9), vatB (3), vatC (6), vga (7) and vgaB (4) conferring resistance to A compounds and the two genes, vgb (8) and vgbB (6), encoding lactonases hydrolyzing B compounds. Nineteen of the strains carried satA and the combination of vat and vgb was detected in a single strain, KH6 (Table 1). These two latter genes are contiguous and in the same relative position as in the staphylococcal plasmids in which vat-vgb are carried by a DNA fragment originating from the *E. faecalis* plasmid, pAMβ1 (5).

Table 1. Relevant characteristics of the 51 *E. faecium* strains isolated in the Netherlands.

| Strain | | $Sg^R$ genes | |
|---|---|---|---|
| designation | Origin (city) | Designation (1) | Size (in kb) of the hybridizing HindIII fragment (2) |
| 4 | pig (Weert) | vatE | 1.8 |
| 14 | pig (Weert) | vatE | 1.8 |
| 17 | pig (Weert) | satA | 4.5* |
| 18 | pig (Weert) | satA | 3.8* |
| 19 | pig (Weert) | satA | 3.8* |
| K12 | turkey | vatE | 6.0* |
| K13 | turkey | vatE | 5.6* |
| K14 | turkey | vatE | 6.0* |
| K15 | turkey | vatE | 5.6* |
| K36 | turkey | satA | 6.0* |
| K40 | turkey | vatE | 3.6* |
| KS30 | turkey | vatE | 1.4 |
| KS31 | turkey | vatE | 1.4 |
| KS33 | turkey | vatE | 1.4 |
| SK1 | broiler | vatE | 3.2* |
| SK2 | broiler | vatE | 3.2* |
| SK3 | broiler | vatE | >10* |
| SK6 | broiler | satA | 7.0* |
| SK7 | broiler | vatE | 5.6* |
| SK8 | broiler | vatE | 5.6* |
| SK13 | broiler | vatE | 3.2* |
| SK19 | broiler | vatE | 3.9* |
| PS17 | broiler | vatE | 4.3* |
| PS22 | broiler | satA | 4.0* |
| PS26 | broiler | vatE | 4.3* |
| PS35 | broiler | vatE | 4.3* |
| PS42 | broiler | vatE | 4.3* |
| KH2 | turkey farmer | vatE | 5.6* |
| KH4 | turkey farmer | satA | 3.9* |
| KH5 | turkey farmer | vatE | 7.3* |
| KH6 | turkey farmer | vatE | 5.6* |
| | | vat-vgb | 8.9 |
| KH7 | turkey farmer | vatE | 2.5 |
| KH15 | turkey farmer | satA | 2.3* |
| KH18 | turkey farmer | vatE | 2.3 |
| KH19 | turkey farmer | vatE | 2.3 |
| KH29 | turkey farmer | vatE | 2.3* |
| KH36 | turkey farmer | satA | 3.9 |
| KH39 | turkey farmer | vatE | 2.9 |
| LKH2 | chicken farmer | satA | 4.0* |
| LKH4 | chicken farmer | satA | 4.3* |
| SKH4 | chicken farmer | vatE | 2.5* |
| SKH8 | chicken farmer | satA | 5.6* |
| SKH11 | chicken farmer | vatE | 2.5 |
| SKH16 | chicken farmer | satA | 4.5* |
| SKH18 | chicken farmer | satA | 3.9* |
| SKH23 | chicken farmer | satA | 3.9* |
| M2 | Suburban (Weert) | satA | 3.9* |
| M5 | suburban (Weert) | vatE | 1.9 |
| R2 | suburban (Roermond) | satA | 3.9* |
| R24 | suburban (Roermond) | satA | 3.9* |
| W3 | suburban (Weert) | satA | 4.0* |

(1) The strains were screened for $Sg^R$ genes by hybridization at high annealing temperature (65° C.) (2) with probe consisting of (i) recombinant plasmids containing DNA inserts from within each of the following genes: vat(9), vatB (3), vatC (6), vga (7) or vgaB (4) or (ii) DNA fragments amplified from satA (18) or vatE (this study) by PCR with the following pairs of primers: sat1 (nt position: 189–210 in satA, Acc. No. L12033) and sat2 (nt position: 760–782 in sat_or vatE-F (nt position: 354–378 in vatE, Acc. No. AF153312) and vatE-R (nt position: 878–899 in vatE).

(2) The HindIII fragments indicated with an asterisk were detected in extrachromosomal DNA bands (≧40 kb) migrating above the chromosomal DNA fragments of the uncleaved total cellular DNA, in agarose gel electrophoresis in Tr-acetate buffer. In the other strains, the hybridizing bands comigrated with the chromosomal fragments, but the hybridization signals were as strong as those of the extra-chromosomal DNA, suggesting that they may be carried plasmids.

Thirty-one of the tested *E. faecium* strains did not contain any of the eight genes investigated. PCR experiments were carried out at low annealing temperature (40° C.) with a pair of degenerate primers, M and N (3, 16), designed to amplify a DNA fragment from any sequence encoding a streptogramin A acetyltransferase containing two well conserved motifs, III and IV (3, 6, 16). A DNA fragment of the expected size (147 nt) was amplified from the cellular DNA of all the strains. The amplicon obtained with the strain K14 was sequenced using oligonucleotides M and N as primers. Its sequence was only 60.4% to 68.6% similar to the SgA acetyltransferase genes (vat, vatB, vatC, satA), suggesting that the amplicon was from a different gene. A 5 kb HindIII fragment hybridizing with the sequenced amplicon was isolated from the cellular DNA of strain K14 and inserted into the HindIII site of pUC18. The resulting plasmid, pIP1798, was used to sequence 1080 nt of the insert including the sequences hybridizing with the 147 bp amplicon.

The sequence (registered in the GenBank EMBL data Library under Accession No. AF153312) contains a 642 bp gene including an ATG start codon preceded, 6 nt upstream, by a putative ribosome-binding site. The free energy of association of the most stable structure between this site and the 3' terminus of the 16S rRNA was −61.5 kj/mol. This gene, named vatE, is similar to those encoding SgA acetyltranferases, satA, vat, vatB, and vatC (54.3, 58.0, 60.0, and 60.1% similarity, respectively). vatE encodes a putative 214 aa protein of 23,775 Da similar to xenobiotic acetyltranferases (17). It is most similar to the SgA acetyltranferases, SatA, Vat, VatB, and VatC (48.5, 50.0, 59.9 and 50.9% identical amino acids, respectively).

Most vat-related genes in staphylococcal plasmids are contiguous to and downstream from another streptogramin-resistance (Sg$^R$) gene. The pairs of genes are probably co-transcribed (12). However, analysis of the 270 and 170 nt sequences flanking vatE did not suggest the presence of any contiguous Sg$^R$ gene.

A DNA fragment of 858 nt containing vatE (nt 104 to nt 961, Accession No. AF153312) was amplified from pIP1798 and inserted between the EcoRI and SmaI sites of the shuttle vector, pOX7 (11). The resulting plasmid, pIP1801, introduced by electroporation in the S. aureus recipient, RN4220 (15), conferred resistance to pristinamycin IIA (MICs: 2 µg/ml for RN4220 [pOX7] and 8 µg/ml for RN4220 [pIP1801]).

The presence of vatE in other strains was tested by hybridization experiments at high stringency. Nucleotide sequences hybridizing with vatE-probe were detected in the 32 strains which did not carry satA, including the strain containing vat-vgb (Table 1). Total cellular DNA of strain KH6 was subjected to agarose gel electrophoresis. The vatE and vat-vgb sequences migrated to different positions, suggesting that they are not carried by the same plasmid.

The distribution of the streptogramin-resistance genes in the collection of E. faecium studied was clearly different from that found in staphylococci (2). It is worth checking whether the high prevalence of vatE in this collection, is also observed among infectious clinical isolates.

In summary, the present invention pertains to polynucleotides derived from Enterococcus faecium genes encoding resistance to streptogramin A and chemically related compounds. This invention also relates to the use of the polynucleotides as oligonucleotide primers or probes for detecting Enterococcus faecium strains that are resistant to streptogramin A and related compounds in a biological sample.

In another embodiment, the present invention is directed to the full length coding sequences of the Enterococcus faecium genes encoding for resistance to streptogramin A and to the polypeptides expressed by these full length coding sequences.

Further, this invention relates to the use of the expressed polypeptides to produce specific monoclonal or polyclonal antibodies that serve as detection means in order to characterize any Enterococcus faecium strain carrying genes encoding resistance to streptogramin A and chemically related compounds.

The present invention is also directed to diagnostic methods for detecting specific strains of Enterococcus faecium expected to be contained in a biological sample. The diagnostic methods use the oligonucleotide probes and primers as well as the antibodies of the invention raised against VatE protein or its fragments.

The invention relates also to a method of screening of molecules, which are capable to inactivate the acetyl transferase activity in bacteria. A bacterial culture, which is resistant to virginiamycin A, can grow in the presence of virginiamycin, but cannot grow if a new molecule active against acetyl transferase activity is added to the culture medium.

REFERENCES

The following publications are cited herein. The entire disclosure of each publication is relied upon and incorporated by reference herein.

1. Aarestrup, F. M., F. Bager, N. E. Jensen, M. Madsen. A. Meyling, and H. C. Wegener. 1998. Surveillance of antimicrobial resistance in bacteria isolated from food animals to antimicrobial growth promoters and related therapeutic agents in Denmark. APMIS 106:606–622.
2. Allignet, J., S. Aubert, A. Morvan, and N. El Solh. 1996. Distribution of the genes encoding resistance to streptogramin A and related compounds among the staphylococci resistant to these antibiotics. Antimicrob. Agents Chemother. 40:2523–2528.
3. Allignet, J., and N. El Solh. 1995. Diversity among the Gram-positive acetyltranferases inactivating streptogramin A and structurally related compounds, and characterization of a new staphylococcal determinant, vatB. Antimicrob. Agents Chemother. 39:2027–2036.
4. Allignet, J., and N. El Solh. 1997. Characterization of a new staphylococcal gene, vgaB, encoding a putative ABC transporter conferring resistance to streptogramin A and related compounds. Gene 202:133–138.
5. Allignet, J., and N. El Solh. 1999. Comparative analysis of staphylococcal plasmids carrying three streptogramin-resistance genes: vat-vgb-vga. Plasmid.
6. Allignet, J., N. Liassine, and N. El Solh. 1998. Characterization of a staphylococcal plasmid related to pUB110, pIP1714, and carrying two novel genes, vatC and vgbB, encoding resistance to streptogramins A and B and similar antibiotics. Antimicrob. Agents Chemother. 42:1794–1798.
7. Allignet, J., V. Loncle, and N. El Solh. 1992. Sequence of a staphylococcal plasmid gene, vga, encoding a putative ATP-binding protein involved in resistance to virginiamycin A-like antibiotics. Gene 117:45–51.
8. Allignet, J., V. Loncle, P. Mazodier, and N. El Solh. 1988. Nucleotide sequence of a staphylococcal plasmid gene, vgb, encoding a hydrolase inactivating the B components of virginiamycin-like antibiotics. Plasmid 20:271–275.
9. Allignet, J., V. Loncle, C. Simenel, M. Delepierre, and N. El Solh. 1993. Sequence of a staphylococcal gene, vat, encoding an acetyltransferase inactivating the A-type compounds of virginiamycin-like antibiotics. Gene 130:91–98.
10. Cocito, C., M. Digambattista, E. Nyssen, and P. Vannuffel. 1997. Inhibition of protein synthesis by streptogramins and related antibiotics. J. Antimicrob. Chemother. 39 (Suppl. A):7–13.
11. Dyke, K., and S. Curnock. 1989. The nucleotide sequence of a small cryptic plasmid found in Staphylococcus aureus and its relationship to other plasmids. FEMS Microbiol. Lett. 58:209–216.
12. El Solh, N., and J. Allignet. 1998. Staphylococcal resistance to streptogramins and related antibiotics. Drug Resist. Updates 1:169–175.
13. Hammerum, A. M., L. B. Jensen, and F. M. Aarestrup. 1998. Detection of the satA gene and transferability of virginiamycin resistance in Enterococcus faecium from food-animals. FEMS Microbiol. Lett. 168:145–151.
14. Jensen, L. B., A. M. Hammerum, F. M. Aarestrup, A. E. van den Bogaard, and E. E. Stobberingh. 1998. Occurrence of sat and vgb genes in streptogramin-resistant Enterococcus faecium isolates of animal and human origins in The Netherlands. Antimicrob. Agents Chemother. 42:3330–3331.
15. Kreiswirth, B. N., S. Lofdahl, M. J. Betley, M. OŌReilly, P. ĒM. ĒShlievert, M. S. Bergdoll, and R. P. Novick. 1983. The toxic shock exotoxin structural gene is not detectably transmitted by a prophage. Nature 306:709–712.
16. Liassine, N., J. Allignet, A. Morvan, S. Aubert, and N. El Solh. 1997. Analysis of pristinamycin-resistant staphylococci selected in an Algerian hospital by the extensive and inappropriate use of pristinamycin (Pt). Zbl. Bakt. 286:389–399.

17. Murray, I. A., and W. V. Shaw. 1997. O-acetyltranferases for chloramphenicol and other natural products. Antimicrob. Agents Chemother. 41:1–6.

18. Rende-Fournier, R., R. Leclercq, M. Galimand, J. Duval, and P.E̅Courvalin. 1993. Identification of the satA gene encoding a streptogramin A acetyltransferase in *Enterococcus faecium* BM4145. Antimicrob. Agents Chemother. 37:2119–2125.

19. van den Bogaard, A. E., P. Mertens, N. H. London, and E.E̅E.E̅Stobberingh. 1997. High prevalence of colonization with vancomycin- and pristinamycin-resistant enterococci in healthy humans and pigs in The Netherlands: is the addition of antibiotics to animal feeds to blame? J. Antimicrob. Chemother. 40:454–456.

20. van den Bogaard, A. E., L. B. Jensen, E. Stobberingh. 1997. An identical VRE isolated from a turkey and a farmer. New Eng. J. Med. 337:1558–1559.

21. Welton, L. A., L. A. Thal, M. B. Perri, S. Donabedian, J. McMahon, J. W. Chow, and M. J. Zervos. 1998. Antimicrobial resistance in enterococci isolated from turkey flocks fed virginiamycin. Antimicrob. Agents Chemother. 42:705–708.

What is claimed is:

1. A purified nucleic acid molecule comprising the DNA sequence of SEQ ID NO:2.

2. A purified nucleic acid molecule encoding an amino acid sequence comprising the sequence of SEQ ID NO:1.

3. A purified nucleic acid molecule encoding a an acetyltransferase inactivating streptogramin A (vatE) protein that hybridizes to either strand of a denatured, double-stranded DNA comprising the nucleic acid sequence of any one of claim 1 or 2 under conditions of high stringency.

4. A recombinant vector that directs the expression of a nucleic acid molecule of claim 3.

5. A host cell transfected or transduced with the vector of claim 4.

6. A method for the production of SEQ ID NO:1 comprising culturing a host cell of claim 5 under conditions promoting expression, and recovering the polypeptide from the culture medium.

7. The method of claim 6, wherein the host cell is selected from the group consisting of bacterial cells, yeast cells, plant cells, and animal cells.

8. The plasmid deposited at CNCM under the Accession Number I-2247.

* * * * *

UNITED STATES PATENT AND TRADEMARK OFFICE
CERTIFICATE OF CORRECTION

PATENT NO.    : 6,905,865 B1
DATED         : June 14, 2005
INVENTOR(S)   : Jullen Haroche, Jeanine Allignet and Nevine El Solh It is certified that error appears in the above-identified patent and that said Letters Patent is hereby corrected as shown below:

Title page,
Item [54], Title, "VATE" shoulde read -- vatE --.

Column 32,
Line 63, "encoding a an" should read -- encoding an --.

Signed and Sealed this

Thirtieth Day of August, 2005

JON W. DUDAS
*Director of the United States Patent and Trademark Office*

SEQUENCE LISTING

<160> NUMBER OF SEQ ID NOS: 22

<210> SEQ ID NO 1
<211> LENGTH: 213
<212> TYPE: PRT
<213> ORGANISM: Enterococcus faecium

<400> SEQUENCE: 1

```
Met Thr Ile Pro Asp Ala Asn Ala Ile Tyr His Asn Ser Ala Ile Lys
  1               5                  10                  15

Glu Val Val Phe Ile Lys Asn Val Ile Lys Ser Pro Asn Ile Glu Ile
                 20                  25                  30

Gly Asp Tyr Thr Tyr Tyr Asp Asp Pro Val Asn Pro Thr Asp Phe Glu
             35                  40                  45

Lys His Val Thr His His Tyr Glu Phe Leu Gly Asp Lys Leu Ile Ile
         50                  55                  60

Gly Lys Phe Cys Ser Leu Ala Ser Gly Ile Glu Phe Ile Met Asn Gly
 65                  70                  75                  80

Ala Asn His Val Met Lys Gly Ile Ser Thr Tyr Pro Phe Asn Ile Leu
                 85                  90                  95

Gly Gly Asp Trp Gln Gln Tyr Thr Pro Glu Leu Thr Asp Leu Pro Leu
                100                 105                 110

Lys Gly Asp Thr Val Val Gly Asn Asp Val Trp Phe Gly Gln Asn Val
            115                 120                 125

Thr Val Leu Pro Gly Val Lys Ile Gly Asp Gly Ala Ile Ile Gly Ala
        130                 135                 140

Asn Ser Val Val Thr Lys Asp Val Ala Pro Tyr Thr Ile Val Gly Gly
145                 150                 155                 160

Asn Pro Ile Gln Leu Ile Gly Pro Arg Phe Glu Pro Glu Val Ile Gln
                165                 170                 175

Ala Leu Glu Asn Leu Ala Trp Trp Asn Lys Asp Ile Glu Trp Ile Thr
            180                 185                 190

Ala Asn Val Pro Lys Leu Met Gln Thr Thr Pro Thr Leu Glu Leu Ile
        195                 200                 205

Asn Ser Leu Met Glu
        210
```

<210> SEQ ID NO 2
<211> LENGTH: 642
<212> TYPE: DNA
<213> ORGANISM: Enterococcus faecium

<400> SEQUENCE: 2

```
atgactatac ctgacgcaaa tgcaatctat cataactcag ccatcaaaga ggttgtcttt    60
```

-continued

```
atcaagaacg tgatcaaaag tcccaatatt gaaattgggg actacaccta ttatgatgac    120
ccagtaaatc ccaccgattt tgagaaacac gttacccatc actatgaatt tctaggcgac    180
aaattaatca tcggtaaatt ttgttctctc gccagtggca ttgaatttat catgaacggt    240
gccaaccacg taatgaaagg tatttcgact tatccattta atatattagg tggcgattgg    300
caacaataca ctcctgaact gactgatttg ccgttgaaag gtgatactgt agtcggaaat    360
gacgtgtggt ttgggcaaaa tgtgaccgtc ctaccaggcg taaaaatagg tgacggtgcc    420
attatcggag caaatagtgt tgtaacaaaa gacgtcgctc catatacaat tgtcggtggc    480
aatccaattc aactcatcgg accaagattt gaaccggaag ttattcaagc attagaaaat    540
ctggcatggt ggaataaaga tattgaatgg ataactgcta atgttcctaa actaatgcaa    600
acaacaccca cacttgaatt gataaacagt ttaatggaaa aa                      642
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 3
caatattgga attcgggact acacc                                          25

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 4 ctgttatga attcaagtgt gg                                              22

<210> SEQ ID NO 5
<211> LENGTH: 7
<212> TYPE: PRT
<213> ORGANISM: Enterococcus faecium

<400> SEQUENCE: 5

Ile Met Asn Gly Ala Asn His
 1               5

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: primer
<223> OTHER INFORMATION: "n" bases may be a, t, c or g

<400> SEQUENCE: 6
athatgaayg cnaaycay                                                  18

<210> SEQ ID NO 7
<211> LENGTH: 5
<212> TYPE: PRT
<213> ORGANISM: Enterococcus faecium

<400> SEQUENCE: 7

Gly Asn Asp Val Trp
 1               5

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: primer
<223> OTHER INFORMATION: "n" bases may be a, t, c or g

<400> SEQUENCE: 8
ccanacrtcr ttncc                                                        15

<210> SEQ ID NO 9
<211> LENGTH: 8
<212> TYPE: PRT
<213> ORGANISM: Enterococcus faecium

<400> SEQUENCE: 9

Ala Asn Ala Ile Tyr His Asn Ser
  1               5

<210> SEQ ID NO 10
<211> LENGTH: 24
<212> TYPE: DNA
<213> ORGANISM: Enterococcus faecium

<400> SEQUENCE: 10
gcaaatgcaa tctatcataa ctca                                              24

<210> SEQ ID NO 11
<211> LENGTH: 9
<212> TYPE: PRT
<213> ORGANISM: Enterococcus faecium

<400> SEQUENCE: 11

Met Gln Thr Thr Pro Thr Leu Glu Leu
  1               5

<210> SEQ ID NO 12
<211> LENGTH: 27
<212> TYPE: DNA
<213> ORGANISM: Enterococcus faecium

<400> SEQUENCE: 12
atgcaaacaa cacccacact tgaattg                                           27

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 13
tagaaagaat tcagtgattg tgg                                               23

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 14
ggattcacta aatagtaaag gccgtg                                            26

<210> SEQ ID NO 15
<211> LENGTH: 840
<212> TYPE: DNA
<213> ORGANISM: Enterococcus faecium

<400> SEQUENCE: 15

| | | | | | |
|---|---|---|---|---|---|
| aaatttaggc | gcacaaaaag | aaagagtgtg | acaaaacatg | gttatgctac | atgtttaagg | 60 |
| taaaaatagt | tatgtcacaa | ctacttattt | ttttacccaa | tcttctagac | tataattaaa | 120 |
| attaaataac | tcaattcgga | ggtactaacc | tgactatacc | tgacgcaaat | gcaatctatc | 180 |
| ataactcagc | catcaaagag | gttgacttta | tcaagaacgt | gatcaaaagt | cccaatattg | 240 |
| aaattgggga | ctacacctat | tatgatgacc | cagtaaatcc | caccgatttt | gagaaacacg | 300 |
| ttacccatca | ctatgaattt | ctaggcgaca | aattaatcat | cggtaaattt | tgttctctcg | 360 |
| ccagtggcat | tgaatttatc | atgaacggtg | ccaaccacgt | aatgaaaggt | atttcgactt | 420 |
| atccatttaa | tatattaggt | ggcgattggc | aacaatacac | tcctgaactg | actgatttgc | 480 |
| cgttgaaagg | tgatactgta | gtcggaaatg | acgtgtggtt | tgggcaaaat | gtgaccgtcc | 540 |
| taccaggcgt | aaaaataggt | gacggtgcca | ttatcggagc | aaatagtgtt | gtaacaaaag | 600 |
| acgtcgctcc | atatacaatt | gtcggtggca | atccaattca | actcatcgga | ccaagatttg | 660 |
| aaccggaagt | tattcaagca | ttagaaaatc | tggcatggtg | gaataaagat | attgaatgga | 720 |
| taactgctaa | tgttcctaaa | ctaatgcaaa | caacacccac | acttgaattg | ataaacagtt | 780 |
| taatggaaaa | ataaaaacaa | aaaagccgtg | caagcaatcc | aaaaatgatt | gtttacacgg | 840 |

<210> SEQ ID NO 16
<211> LENGTH: 44
<212> TYPE: DNA
<213> ORGANISM: Enterococcus faecium

<400> SEQUENCE: 16
tgtcacaact acttattttt ttacccaatc ttctagacta taat        44

<210> SEQ ID NO 17
<211> LENGTH: 1080
<212> TYPE: DNA
<213> ORGANISM: Enterococcus faecium
<220> FEATURE:
<221> NAME/KEY: CDS
<222> LOCATION: (271)..(912)

<400> SEQUENCE: 17

| | | | | | |
|---|---|---|---|---|---|
| ccctttaaag | agggcttta | tatattaatc | acaaatcact | tatcacaaat | cacaagtgat | 60 |
| ttgtgattgt | tgatgataaa | ataagaataa | gaagaaatag | aaagaagtga | gtgattgtgg | 120 |
| gaaatttagg | cgcacaaaaa | gaaagagtgt | gacaaaacat | ggttatgcta | catgtttaag | 180 |
| gtaaaaatag | ttatgtcaca | actacttatt | ttttacccca | atcttctaga | ctataattaa | 240 | aattaaataa ctcaattcgg aggtactaac atg act ata cct gac gca aat gca    294
                  Met Thr Ile Pro Asp Ala Asn Ala
                   1      5 atc tat cat aac tca gcc atc aaa gag gtt gtc ttt atc aag aac gtg    342
Ile Tyr His Asn Ser Ala Ile Lys Glu Val Val Phe Ile Lys Asn Val
  10       15         20 atc aaa agt ccc aat att gaa att ggg gac tac acc tat tat gat gac    390
Ile Lys Ser Pro Asn Ile Glu Ile Gly Asp Tyr Thr Tyr Tyr Asp Asp
25        30         35         40 cca gta aat ccc acc gat ttt gag aaa cac gtt acc cat cac tat gaa    438
Pro Val Asn Pro Thr Asp Phe Glu Lys His Val Thr His His Tyr Glu -continued

```
                  45                  50                  55
ttt cta ggc gac aaa tta atc atc ggt aaa ttt tgt tct ctc gcc agt      486
Phe Leu Gly Asp Lys Leu Ile Ile Gly Lys Phe Cys Ser Leu Ala Ser
                60                  65                  70 ggc att gaa ttt atc atg aac ggt gcc aac cac gta atg aaa ggt att      534
Gly Ile Glu Phe Ile Met Asn Gly Ala Asn His Val Met Lys Gly Ile
            75                  80                  85 tcg act tat cca ttt aat ata tta ggt ggc gat tgg caa caa tac act      582
Ser Thr Tyr Pro Phe Asn Ile Leu Gly Gly Asp Trp Gln Gln Tyr Thr
        90                  95                  100 cct gaa ctg act gat ttg ccg ttg aaa ggt gat act gta gtc gga aat      630
Pro Glu Leu Thr Asp Leu Pro Leu Lys Gly Asp Thr Val Val Gly Asn
105                 110                 115                 120 gac gtg tgg ttt ggg caa aat gtg acc gtc cta cca ggc gta aaa ata      678
Asp Val Trp Phe Gly Gln Asn Val Thr Val Leu Pro Gly Val Lys Ile
                125                 130                 135 ggt gac ggt gcc att atc gga gca aat agt gtt gta aca aaa gac gtc      726
Gly Asp Gly Ala Ile Ile Gly Ala Asn Ser Val Val Thr Lys Asp Val
            140                 145                 150 gct cca tat aca att gtc ggt ggc aat cca att caa ctc atc gga cca      774
Ala Pro Tyr Thr Ile Val Gly Gly Asn Pro Ile Gln Leu Ile Gly Pro
        155                 160                 165 aga ttt gaa ccg gaa gtt att caa gca tta gaa aat ctg gca tgg tgg      822
Arg Phe Glu Pro Glu Val Ile Gln Ala Leu Glu Asn Leu Ala Trp Trp
170                 175                 180 aat aaa gat att gaa tgg ata act gct aat gtt cct aaa cta atg caa      870
Asn Lys Asp Ile Glu Trp Ile Thr Ala Asn Val Pro Lys Leu Met Gln
185                 190                 195                 200 aca aca ccc aca ctt gaa ttg ata aac agt tta atg gaa aaa              912
Thr Thr Pro Thr Leu Glu Leu Ile Asn Ser Leu Met Glu Lys
                205                 210 taaaaacaaa aaagccgtgc aagcaatcca aaaatgattg tttacacggc ctttactatt    972
tagtgaatcc aatttattaa taatagatat gatataccag taaaaaatac actagccacc  1032
tctggcggta ctctactcgt atattttatt tacgaccttc tgatgata                1080
```

<210> SEQ ID NO 18
<211> LENGTH: 214
<212> TYPE: PRT
<213> ORGANISM: Enterococcus faecium

<400> SEQUENCE: 18

```
Met Thr Ile Pro Asp Ala Asn Ala Ile Tyr His Asn Ser Ala Ile Lys
1               5                   10                  15

Glu Val Val Phe Ile Lys Asn Val Ile Lys Ser Pro Asn Ile Glu Ile
            20                  25                  30

Gly Asp Tyr Thr Tyr Tyr Asp Pro Val Asn Pro Thr Asp Phe Glu
        35                  40                  45

Lys His Val Thr His His Tyr Glu Phe Leu Gly Asp Lys Leu Ile Ile
    50                  55                  60

Gly Lys Phe Cys Ser Leu Ala Ser Gly Ile Glu Phe Ile Met Asn Gly
65                  70                  75                  80

Ala Asn His Val Met Lys Gly Ile Ser Thr Tyr Pro Phe Asn Ile Leu
                85                  90                  95

Gly Gly Asp Trp Gln Gln Tyr Thr Pro Glu Leu Thr Asp Leu Pro Leu
            100                 105                 110

Lys Gly Asp Thr Val Val Gly Asn Asp Val Trp Phe Gly Gln Asn Val
        115                 120                 125
```

```
Thr Val Leu Pro Gly Val Lys Ile Gly Asp Gly Ala Ile Ile Gly Ala
    130                 135                 140

Asn Ser Val Val Thr Lys Asp Val Ala Pro Tyr Thr Ile Val Gly Gly
145                 150                 155                 160

Asn Pro Ile Gln Leu Ile Gly Pro Arg Phe Glu Pro Glu Val Ile Gln
                165                 170                 175

Ala Leu Glu Asn Leu Ala Trp Trp Asn Lys Asp Ile Glu Trp Ile Thr
            180                 185                 190

Ala Asn Val Pro Lys Leu Met Gln Thr Thr Pro Thr Leu Glu Leu Ile
        195                 200                 205

Asn Ser Leu Met Glu Lys
    210

<210> SEQ ID NO 19
<211> LENGTH: 219
<212> TYPE: PRT
<213> ORGANISM: Unknown Organism
<220> FEATURE:
<223> OTHER INFORMATION: Description of Unknown Organism:
      acetyltransferase enzyme

<400> SEQUENCE: 19

Leu Asn Leu Asn Asn Asp His Gly Pro Asp Pro Glu Asn Ile Leu Pro
 1               5                  10                  15

Ile Lys Gly Asn Arg Asn Leu Gln Phe Ile Lys Pro Thr Ile Thr Asn
                20                  25                  30

Glu Asn Ile Leu Val Gly Glu Tyr Ser Tyr Asp Ser Lys Arg Gly
            35                  40                  45

Glu Ser Phe Glu Asp Gln Val Leu Tyr His Tyr Glu Val Ile Gly Asp
     50                  55                  60

Lys Leu Ile Ile Gly Arg Phe Cys Ser Ile Gly Pro Gly Thr Thr Phe
 65                  70                  75                  80

Ile Met Asn Gly Ala Asn His Arg Met Asp Gly Ser Thr Tyr Pro Phe
                85                  90                  95

His Leu Phe Arg Met Gly Trp Glu Lys Tyr Met Pro Ser Leu Lys Asp
                100                 105                 110

Leu Pro Leu Lys Gly Asp Ile Glu Ile Gly Asn Asp Val Trp Ile Gly
            115                 120                 125

Arg Asp Val Thr Ile Met Pro Gly Val Lys Ile Gly Asp Gly Ala Ile
    130                 135                 140

Ile Ala Ala Glu Ala Val Val Thr Lys Asn Val Ala Pro Tyr Ser Ile
145                 150                 155                 160

Val Gly Gly Asn Pro Leu Lys Phe Ile Arg Lys Arg Phe Ser Asp Gly
                165                 170                 175

Val Ile Glu Glu Trp Leu Ala Leu Gln Trp Trp Asn Leu Asp Met Lys
            180                 185                 190

Ile Ile Asn Glu Asn Leu Pro Phe Ile Ile Asn Gly Asp Ile Glu Met
        195                 200                 205

Leu Lys Arg Lys Arg Lys Leu Leu Asp Asp Thr
    210                 215

<210> SEQ ID NO 20
<211> LENGTH: 212
<212> TYPE: PRT
<213> ORGANISM: Unknown Organism
<220> FEATURE:
<223> OTHER INFORMATION: Description of Unknown Organism:
``` acetyltransferase enzyme

<400> SEQUENCE: 20

```
Met Lys Trp Gln Asn Gln Gly Pro Asn Pro Glu Ile Tyr Pro
 1               5                  10                  15

Ile Glu Gly Asn Lys His Val Gln Phe Ile Lys Pro Ser Ile Thr Lys
                20                  25                  30

Pro Asn Ile Leu Val Gly Glu Tyr Ser Tyr Tyr Asp Ser Lys Asp Gly
            35                  40                  45

Glu Ser Phe Glu Ser Gln Val Leu Tyr His Tyr Glu Leu Ile Gly Asp
        50                  55                  60

Lys Leu Ile Leu Gly Lys Phe Cys Ser Ile Gly Pro Gly Thr Thr Phe
 65                  70                  75                  80

Ile Met Asn Gly Ala Asn His Arg Met Asp Gly Ser Thr Phe Pro Phe
                85                  90                  95

Asn Leu Phe Gly Asn Gly Trp Glu Lys His Thr Pro Thr Leu Glu Asp
            100                 105                 110

Leu Pro Tyr Lys Gly Asn Thr Glu Ile Gly Asn Asp Val Trp Ile Gly
        115                 120                 125

Arg Asp Val Thr Ile Met Pro Gly Val Lys Ile Gly Asn Gly Ala Ile
    130                 135                 140

Ile Ala Ala Lys Ser Val Val Thr Lys Asn Val Asp Pro Tyr Ser Val
145                 150                 155                 160

Val Gly Gly Asn Pro Ser Arg Leu Ile Lys Ile Arg Phe Ser Lys Glu
                165                 170                 175

Lys Ile Ala Ala Leu Leu Lys Val Arg Trp Trp Asp Leu Glu Ile Glu
            180                 185                 190

Thr Ile Asn Glu Asn Ile Asp Cys Ile Leu Asn Gly Asp Ile Lys Lys
        195                 200                 205

Val Lys Arg Ser
    210
```

<210> SEQ ID NO 21
<211> LENGTH: 209
<212> TYPE: PRT
<213> ORGANISM: Unknown Organism
<220> FEATURE:
<223> OTHER INFORMATION: Description of Unknown Organism:
       acetyltransferase enzyme

<400> SEQUENCE: 21

```
Met Gly Pro Asn Pro Met Lys Met Tyr Pro Ile Glu Gly Asn Lys Ser
 1               5                  10                  15

Val Gln Phe Ile Lys Pro Ile Leu Glu Lys Leu Glu Asn Val Glu Val
                20                  25                  30

Gly Glu Tyr Ser Tyr Tyr Asp Ser Lys Asn Gly Glu Thr Phe Asp Lys
            35                  40                  45

Gln Ile Leu Tyr His Tyr Pro Ile Leu Asn Asp Lys Leu Lys Ile Gly
        50                  55                  60

Lys Phe Cys Ser Ile Gly Pro Gly Val Thr Ile Met Asn Gly Ala
 65                  70                  75                  80

Asn His Arg Met Asp Gly Ser Thr Tyr Pro Phe Asn Leu Phe Gly Asn
                85                  90                  95

Gly Trp Glu Lys His Met Pro Lys Leu Asp Gln Leu Pro Ile Lys Gly
            100                 105                 110

Asp Thr Ile Ile Gly Asn Asp Val Trp Ile Gly Lys Asp Val Val Ile
```

```
                    115                 120                 125
Met Pro Gly Val Lys Ile Gly Asp Gly Ala Ile Val Ala Ala Asn Ser
    130                 135                 140

Val Val Val Lys Asp Ile Ala Pro Tyr Met Leu Ala Gly Gly Asn Pro
145                 150                 155                 160

Ala Asn Glu Ile Lys Gln Arg Phe Asp Gln Asp Thr Ile Asn Gln Leu
                165                 170                 175

Leu Asp Ile Lys Trp Trp Asn Trp Pro Ile Asp Ile Ile Asn Glu Asn
                180                 185                 190

Ile Asp Lys Ile Leu Asp Asn Ser Ile Ile Arg Glu Val Ile Trp Lys
                195                 200                 205

Lys

<210> SEQ ID NO 22
<211> LENGTH: 212
<212> TYPE: PRT
<213> ORGANISM: Unknown Organism
<220> FEATURE:
<223> OTHER INFORMATION: Description of Unknown Organism:
      acetyltransferase enzyme

<400> SEQUENCE: 22

Met Lys Tyr Gly Pro Asp Pro Asn Ser Ile Tyr Pro His Glu Glu Ile
  1               5                  10                  15

Lys Ser Val Cys Phe Ile Lys Asn Thr Ile Thr Asn Pro Asn Ile Ile
                 20                  25                  30

Val Gly Asp Tyr Thr Tyr Tyr Ser Asp Val Asn Gly Ala Glu Lys Phe
             35                  40                  45

Glu Glu His Val Thr His His Tyr Glu Phe Arg Gly Asp Lys Leu Val
         50                  55                  60

Ile Gly Lys Phe Cys Ala Ile Ala Glu Gly Ile Glu Phe Ile Met Asn
 65                  70                  75                  80

Gly Ala Asn His Arg Met Asn Ser Ile Thr Thr Tyr Pro Phe Asn Ile
                 85                  90                  95

Met Gly Asn Gly Trp Glu Lys Ala Thr Pro Ser Leu Glu Asp Leu Pro
                100                 105                 110

Phe Lys Gly Asp Thr Val Val Gly Asn Asp Val Trp Ile Gly Gln Asn
                115                 120                 125

Val Thr Val Met Pro Gly Ile Gln Ile Gly Asp Gly Ala Ile Val Ala
    130                 135                 140

Ala Asn Ser Val Val Thr Lys Asp Val Pro Pro Tyr Arg Ile Ile Gly
145                 150                 155                 160

Gly Asn Pro Ser Arg Ile Ile Lys Lys Arg Phe Glu Asp Glu Leu Ile
                165                 170                 175

Asp Tyr Leu Leu Gln Ile Lys Trp Trp Asp Trp Ser Ala Gln Lys Ile
                180                 185                 190

Phe Ser Asn Leu Glu Thr Leu Cys Ser Ser Asp Leu Glu Lys Ile Lys
                195                 200                 205

Ser Ile Arg Asp
    210
```